ис010314885B2

(12) United States Patent
Feifel

(10) Patent No.: US 10,314,885 B2
(45) Date of Patent: Jun. 11, 2019

(54) OXYTOCIN TREATMENT TO MODIFY BLOOD GLUCOSE AND TREAT METABOLIC DISEASE

(71) Applicant: The Regents of the University of California, Oakland, CA (US)

(72) Inventor: David Feifel, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 31 days.

(21) Appl. No.: 15/445,816

(22) Filed: Feb. 28, 2017

(65) Prior Publication Data
US 2017/0224763 A1 Aug. 10, 2017

Related U.S. Application Data

(62) Division of application No. 13/812,850, filed as application No. PCT/US2011/046046 on Jul. 30, 2011, now Pat. No. 9,585,935.

(60) Provisional application No. 61/369,607, filed on Jul. 30, 2010.

(51) Int. Cl.
*A61K 9/00* (2006.01)
*A61K 38/095* (2019.01)

(52) U.S. Cl.
CPC .......... *A61K 38/095* (2019.01); *A61K 9/0043* (2013.01)

(58) Field of Classification Search
None
See application file for complete search history.

(56) References Cited

U.S. PATENT DOCUMENTS

| 2004/0235956 A1 | 11/2004 | Quay |
| 2007/0117794 A1 | 5/2007 | Rahman |

FOREIGN PATENT DOCUMENTS

| WO | 98/43661 | 10/1998 | |
| WO | 2008/150305 A1 | 12/2008 | |
| WO | WO 2009/043458 | * 4/2009 | ............. A61K 38/11 |

OTHER PUBLICATIONS

De Hert et al., European Psychiatry, 2009; 24: 412-424 (Year: 2009).*
Cai et al., Drug Discov Today Dis Mech. Jun. 1, 2013; 10(1-2): e63-e68. doi:10.1016/j.ddmec.2013.05.006 (Year: 2013).*
Ott et al., Diabetes, 2013; 62: 3418-3425 (Year: 2013).*
Zhang et al. 2013; PLoS One 8(5): e61477. doi:10.1371/journal.pone.0061477 (Year: 2013).*
Altszuler and Hamphsire, Proceedings of the Society for Experimental Biology and Medicine, 1981; 168, 123-124 (Year: 1981).*
Sawyer and Manning, Annu. Rev. Pharmacol., 1973; 13: 5-17 (Year: 1973).*
Budesinky et al., Protein Pept Lett., 2005; 12: 343-7 (Year: 2005).*
Andreasen, N.C., "The American Concept of Schizophrenia," Schizophrenia Bulletin, 15(4):519-531, 1989.
Bakharev et al., "Psychotropic Properties of Oxytocin", Problemy endokrinologii, Mar.-Apr. 1984, vol. 30, No. 2, pp. 37-41.
Bales et al., "Chronic Intranasal Oxytocin Causes Long-Term Impairments in Partner Preference Formation in Male Prairie Voles", Biological Psychiatry, vol. 74, Issue 3, Aug. 2013, pp. 180-188.
Davis et al., "Effects of single dose intranasal oxytocin on social cognition in schizophrenia", Shizophrenia Research, vol. 147, Issues 2-3, Jul. 2013, pp. 393-397.
Domes et al., "Oxytocin Improves "Mind-Reading" in Humans", Biological Psychiatry, vol. 61, Issue 6, Mar. 15, 2007, pp. 731-733.
DSM-IV-TR, "Schizphrenia and Other Psychotic Disorders," p. 154-155, 2000.
Feifel et al., "Intranasal oxytocin augmentation of antipsychotic medication in schizophrenia patients", Society for Neuroscience Abstract; Oct. 17-21, 2009, vol. 39, Poster 644. 12/U27.
Feifel et al., "Adjunctive Intranasal Oxytocin Reduces Symptoms in Schizophrenia Patients", Biol. Psychiatry, 2010, 68:678-680.
Feifel et al., "Daily Intranasal Oxytocin Improves Memory in Schizophrenia Patients", presented at ACNP 49th Annual Meeting, Dec. 5-9, 2010, Miami Beach, Florida, Abstract #49.
Guastella et al, "A randomized controlled trial of intranasal oxytocin as an adjunct to exposure therapy for social anxiety disorder", Psychoneuroendocrinology, vol. 34, Issue 6, Jul. 2009, pp. 917-923.
Hoffman et al., "Catalepsy as a rodent model for detecting antipsychotic drugs with extrapyramidal side effect liability," Psychopharmacology, 120:128-133, 1995.
Iqbal et al. "Schizophrenia Diagnosis," Psychiatric Annals, 23(3):105-119, Mar. 1993.
Keith et al., "U.S. and Soviet Perspectives on the Diagnosis of Schizophrenia and Associated Dangerousness," Schizophrenia Bulletin, 15(4):515-517, 1989.
Lavretsky, H., "The Russian Concept of Schizophrenia: A Review of the Literature," Schizophrenia Bulletin, 24(4):537-557, 1998.
Lim, Hea Joon, International Search Report and Written Opinion, PCT/US2011/046046, Korean Patent Office, dated Mar. 28, 2012.
Matthysse, S., "Dopamine and the Pharmacology of Schizophrenia: The State of the Evidence," J. Psychiat. Res., 11:107-113, 1974.
Mayo Clinic, "Schizoid personality disorder", The Mayo Clinic website (mayoclinic.org/diseases-conditions/schizoid-personality-disorder/basics/symptoms/con-20029184), downloaded on Sep. 10, 2015; 4 pages total.
Nickitas-Etienne, Athina, International Preliminary Report on Patentability, PCT/US2011/046046, The International Bureau of WIPO, dated Feb. 14, 2013.

(Continued)

*Primary Examiner* — Christina M Borgeest
(74) *Attorney, Agent, or Firm* — Gavrilovich, Dodd & Lindsey LLP

(57) ABSTRACT

The disclosure provides a method for enhancing memory of a subject, lowering blood glucose levels in a subject, and treating schizophrenia, the methods comprise intranasally administering to the subject an amount of a oxytocin peptide or analog thereof having a beneficial effect.

4 Claims, No Drawings
Specification includes a Sequence Listing.

(56) References Cited

OTHER PUBLICATIONS

Pinkham et al., "Affect recognition deficits in schizophrenia: neural substrates and psychopharmacological implications", Expert Review of Neurotherapeutics, vol. 7, Issue 7, 2007, pp. 807-816.

Ring et al., "Receptor and behavioral pharmacology of WAY-267464, a non-peptide oxytocin receptor agonist," Neuropharmacology, 58:69-77, 2010.

Rotzinger et al., "Behavioral effects of neuropeptides in rodent models of depression and anxiety," Peptides, 31:736-756, 2010.

* cited by examiner

SEQUENCE LISTING

<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Cys Tyr Ile Gln Asn Cys Pro Leu Gly
1               5

OXYTOCIN TREATMENT TO MODIFY BLOOD GLUCOSE AND TREAT METABOLIC DISEASE

CROSS REFERENCE TO RELATED APPLICATIONS

This application is a divisional of U.S. patent application Ser. No. 13/812,850, filed May 7, 2013, which is a U.S. National Stage Application filed under 35 U.S.C. § 371 and claims priority to International Application No. PCT/US2011/046046, filed Jul. 30, 2011, which application claims priority under 35 U.S.C. § 119 to U.S. Provisional Application Ser. No. 61/369,607, filed Jul. 30, 2010. The disclosures of which are incorporated herein by reference.

BACKGROUND

Oxytocin and its receptors exist in areas of the brain implicated in the symptoms of schizophrenia such as the nucleus accumbens and the hippocampus. Previous studies have shown that oxytocin administered to humans has a propensity to decrease verbal memory. Studies that have administered a single dose of oxytocin worsened recall for words. (Ferrier et al., Life Sci., 27(24), 1980; Fehm-Wolfsdorf et al., Pscyhoneuroendrocrinology, 9(3):285-92, 1984; Bruins et al., Peptides, 13(3):461-8, 1991; Heinrichs et al., Phsiol. Behav, 83(1):31-8, 2004). In fact one study gave a person with obsessive compulsive disorder intranasal oxytocin for 4 weeks and found that it produced significant worsening of his memory (Ansseau et al, 1987).

SUMMARY

The disclosure provides a method for enhancing memory of a subject, the method comprising intranasally administering to the subject an amount of an oxytocin peptide or analogue thereof wherein the amount of oxytocin peptide or analogue thereof improves a subject's memory compared to the subject before administration of the oxytocin peptide or analogue thereof.

The disclosure also provides a method for reducing blood glucose levels of a subject, the method comprising intranasally administering to the subject an amount of a oxytocin peptide or analogue thereof wherein the amount of oxytocin peptide or analogue thereof reduces a subject's blood glucose compared to the subject's blood glucose before administration of the oxytocin peptide or analogue thereof.

The disclosure provides a method of treating schizophrenia comprising administering intranasally, as an adjunctive therapy, oxytocin or an analogue thereof.

The disclosure provide methods of using an oxytocin formulation for improving psychiatric disorders, memory and blood glucose levels. The disclosure provides use of a formulation for intranasal delivery of an oxytocin peptide chronically for the treatment of a disease or disorder selected from the group consisting of a psychiatric disease or disorder, a metabolic disease or disorder and a memory disease or disorder. In one embodiment, the formulation is delivered at least once per day at a dose of about 20-100 IU. In another embodiment, the dose is at least two times per day at a dose of about 20-100 IU per administration. In yet another embodiment, the dose is about 40-80 IU per day. In one embodiment, the psychiatric disease or disorder is schizophrenia. In another embodiment, the metabolic disease or disorder is diabetes. In yet another embodiment, the use improves non-social memory.

The disclosure also provides a method for enhancing non-social memory in a subject, the method comprising intranasally administering to the subject an amount of a oxytocin peptide or analogue thereof in an amount of about 20-100 IU per day, wherein the amount of oxytocin peptide or analogue thereof improves a subject's non-social memory compared to the subject before administration of the oxytocin peptide or analogue thereof. In one embodiment, the subject has a memory disease or disorder. In yet another embodiment, the subject has a psychiatric disease or disorder that can be improved by improving memory. In yet another embodiment, the subject has schizophrenia. In another embodiment, the oxytocin peptide or analogue is administered at least twice per day. In yet another embodiment, the oxytocin peptide or analogue is administered two-times per day. In a further embodiment, the total daily dose is about 80-100 IU per day.

The disclosure also provides a method of treating a metabolic disorder in a subject, comprising intranasally administering an oxytocin peptide intranasally at a dose of about 20-100 IU per day. In one embodiment, the metabolic disorder is selected from the group consisting of diabetes obesity, hyperlipemia, diabetes, fatty liver, hypertension, and cardiovascular disease.

The disclosure also provides a method for reducing blood glucose levels of a subject, the method comprising intranasally administering to the subject an amount of a oxytocin peptide or analogue thereof wherein the amount of oxytocin peptide or analogue thereof reduces a subject's blood glucose compared to the subject's blood glucose before administration of the oxytocin peptide or analogue thereof.

In any of the foregoing embodiment, the oxytocin peptide or analogue thereof is a peptide with at least about 75%, 80%, 85%, 90%, 95%, 97% or 99% identity to SEQ ID NO:1 and wherein the oxytocin peptide or analogue thereof improves memory or reduces blood glucose.

The details of one or more embodiments of the disclosure are set forth in the accompanying drawings and the description below. Other features, objects, and advantages will be apparent from the description and drawings, and from the claims.

DETAILED DESCRIPTION

As used herein and in the appended claims, the singular forms "a," "and," and "the" include plural referents unless the context clearly dictates otherwise. Thus, for example, reference to "a peptide" includes a plurality of such peptides and reference to "the cell" includes reference to one or more cells known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Oxytocin is a nine amino acid cyclic peptide hormone with two cysteine residues that form a disulfide bridge between positions 1 and 6. Human oxytocin comprises the sequence Cys-Tyr-Ile-Gln-Asn-Cys-Pro-Leu-Gly (SEQ ID NO:1). Oxytocin is released from the pituitary gland and stimulates the contraction of smooth muscle of the uterus during labor and facilitates release of milk from the breast during nursing. Oxytocin has historically been used to induce labor.

As used herein, "oxytocin" or "oxytocin peptide" refers to a substance having biological activity associated with natural oxytocin. Oxytocin or oxytocin peptide can be a naturally occurring endogenous peptide, fragments, analogues or derivatives thereof. Oxytocin or oxytocin peptide can also be a non-endogenous peptide, fragments, analogues or derivatives thereof. An oxytocin peptide includes both natural or synthetic, therapeutically or prophylactically active, peptide fragments, peptide analogues, and chemically modified derivatives or salts of active peptides. There are processes described for the production of oxytocin, see for example U.S. Pat. Nos. 2,938,891 and 3,076,797. In addition, oxytocin is commercially available. A variety of peptide analogues and derivatives are available and others can be contemplated for use within the disclosure and can be produced and tested for biological activity according to known methods. Oxytocin analogues may included, but are not limited to, 4-threonine-1-hydroxy-deaminooxytocin, 4-serine, 8-isoleucine-oxytocin, 9-deamidooxytocin, 7-D-proline-oxytocin and its deamino analog, (2,4-diisoleucine)-oxytocin, deamino oxytocin analog, 1-deamino-1-monocarba-E12-Tyr(OMe)]-OT(dCOMOT), carbetocin, 4-threonine, 7-glycine-oxytocin (TG-OT), oxypressin, deamino-6-carba-oxytoxin (dC60), deamino-1 monocarba-(2-O-methyltyrosine)-oxytocin [d(COMOT)]); [Thr4-Gly7]-oxytocin (TG-OT); oxypressin; Ile-conopressin; atosiban; deamino-6-carba-oxytoxin (dC60), d[Lys(8)(5/6C-Fluorescein)]VT, d[Thr(4), Lys(8)(5/6C-Fluorescein)]VT, [HO(1)][Lys(8)(5/6C-Fluorescein)]VT, [HO(1)][Thr(4), Lys(8)(5/6CFluorescein)]VT, d[Orn(8)(5/6C-Fluorescein)]VT, d[Thr(4), Orn(8)(5/6C-Fluorescein)]VT, [HO(1)][Orn(8)(5/6C-Fluorescein)]VT, [HO(I)][Thr(4), Orn(8)(5/6C-Fluorescein)]VT, desmopressin, and 1-deamino-oxytocin in which the disulfide bridge between residues 1 and 6 is replaced by a thioether, L-371,257 and the related series of compounds containing an ortho-trigluoroethoxyphenylacetyl core such as L-374,943. Oxytocin peptide and polypeptide useful in the methods and compositions of the disclosure include peptides that are obtainable by partial substitution, addition, or deletion of amino acids within a naturally occurring or native peptide sequence.

As used herein, "analogues and derivatives" refers to any peptide analogous of naturally occurring oxytocin wherein one or more amino acids within the peptide have been substituted, deleted, or inserted. The term also refers to any peptide wherein one or more amino acids have been modified, for example by chemical modification. In general, the term covers all peptides which exhibit oxytocin activity but which may, if desired, have a different potency or pharmacological profile. Peptides can be chemically modified, for example, by amidation of the carboxyl terminus (—NH$_2$), the use of D amino acids in the peptide, incorporation of small non-peptidyl moieties, as well as the modification of the amino acids themselves (e.g., alkylation or esterification of side chain R-groups). Such analogues, derivatives and fragments should substantially retain the desired biological activity of the native oxytocin peptide.

In still other embodiments the oxytocin analogs are fragments of oxytocin, for example, peptide cleavage products. Such fragments may be chemically synthesized or derived by any known means. Oxytocin fragments of the disclosure retain bioactivity similar to or greater than oxytocin. Such fragments may be capable of crossing the blood brain barrier.

In another embodiment of the disclosure, oxytocin analogs are synthetic oxytocin molecules that retain oxytocin bioactivity. Such analog molecules are capable of acting in a manner similar to endogenous oxytocin, including binding the oxytocin receptor. Analogs of this type may be derivatives of oxytocin or have completely new molecular structures.

In another embodiment oxytocin analogs can be modified for increased stability, enhancement of transport across the blood brain barrier, retention in the brain once they have crossed the blood brain barrier or a combination of the foregoing. Modifications to increase stability and enhance blood brain barrier transport may include, but are not limited to, esterification with steroids, such as cholesteryl, or esterification with fatty alcohols, such as C-8 to C-22 alcohols. Modifications to increase retention in the brain include, but are not limited to, covalent attachment of 1,4-dihydrotrigonellinate and other redox sensitive functionalities, such as quinones and derivatives such as benzoquinones, naphthoquinones, indolequinones, nitroheterocycles such as nitrobenzyl, nitrofurans, and nitroimadzole derivatives.

The peptides/polypeptides described and/or contemplated herein can be prepared by chemical synthesis using either automated or manual solid phase synthetic technologies, generally known in the art. The peptides can also be prepared using molecular recombinant techniques known in the art.

A polypeptide or peptide of the disclosure may be prepared by culturing transformed host cells under culture conditions suitable to express the recombinant polypeptide. The resulting expressed polypeptide may then be purified from such culture (e.g., from culture medium or cell extracts) using known purification processes, such as gel filtration and ion exchange chromatography. The purification of a polypeptide may also include an affinity column containing agents which will bind to the polypeptide; one or more column steps over such affinity resins as concanavalin A-agarose, Heparin-Toyopearl or Cibacrom blue 3GA Sepharose; one or more steps involving hydrophobic interaction chromatography using such resins as phenyl ether, butyl ether, or propyl ether; or immunoaffinity chromatography. Alternatively, a polypeptide of the disclosure may also be expressed in a form that will facilitate purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. A polypeptide can also be tagged with an epitope and subsequently purified by using a specific antibody directed to such epitope. One such epitope ("Flag") is commercially available. Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous isolated recombinant polypeptide. A polypeptide thus purified is substantially free of other mammalian polypeptides and is defined in accordance with the disclosure as a "substantially purified polypeptide. A polypeptide of the disclosure may also be expressed as a product of transgenic animals, e.g., as a component of the milk of transgenic cows, goats, pigs, or sheep which are characterized by somatic or germ cells containing a polynucleotide encoding the polypeptide.

It is also possible to utilize an affinity column comprising a monoclonal antibody generated against an oxytocin peptide of the disclosure, to affinity-purify an expressed polypeptide. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the disclosure. In this embodiment of the disclosure, an anti-polypeptide antibody of the disclosure or other polypeptides that can interact with a polypeptide of the disclosure, can be bound to a solid phase support such as a column chromatography matrix or a similar substrate suitable for identifying, separating, or purifying cells that express polypeptides of the disclosure on their surface.

A polypeptide may also be produced by known conventional chemical synthesis. Methods for constructing polypeptides of the disclosure by synthetic means are known to those skilled in the art. The synthetically constructed polypeptides, by virtue of sharing primary, secondary or tertiary structural and/or conformational characteristics with native polypeptides may possess biological properties in common therewith, including polypeptide activity. Thus, they may be employed as biologically active or immunological substitutes for natural, purified polypeptides in screening of therapeutic compounds and in immunological processes for the development of antibodies.

The desired degree of purity depends on the intended use of a polypeptide. A relatively high degree of purity is desired when a polypeptide is to be administered in vivo, for example. In such a case, polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. A polypeptide of the disclosure is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Schizophrenia is a crippling, clinically heterogeneous disease that afflicts patients with hallucinations and delusions as well as profound impairments in social and executive function. Current medication treatments for schizophrenia, though they significantly alleviate some of these symptoms, fall short of the goal of remission in a large majority of cases. As such, finding novel treatments that impact the broad range of symptoms of schizophrenia is an urgent priority.

In particular, deficits in cognitive function—a particularly disabling component of schizophrenia-are at best partially ameliorated with current antipsychotic medications. This shortcoming is notable, as these deficits often predict patient's level of dysfunction. Cognitive deficits include problems with attention and goal-initiation, as well as impairments in several types of memory. Though there have been efforts to develop psychopharmacologic treatments to address this cluster of symptoms, no current antipsychotic medications decisively improve this domain of function.

The disclosure provides a method of treating schizophrenia comprising delivering oxytocin peptide intranasally to a subject. The oxytocin peptide may be a naturally occurring purified form of oxytocin, a recombinant for of oxytocin and analog of oxytocin, a chemically modified form of oxytocin or a combination thereof. The intranasal delivery improves uptake, compliance and treatment of schizophrenia. In one embodiment, the method comprises delivery an oxytocin peptide intranasally at least twice per day. In another embodiment, the oxytocin peptide is delivered at least twice per day at a dose of about 20-50 IU (international units) per administration (e.g., about 40-100 IU per day). Doses may range from about 10-80 IU per administration and will depend upon various factors readily identifiable to a physician (e.g., body weight, route of administration, formulation, severity of a disease or disorder and the like). Accordingly, the total dose for a subject may be about 20-160 (e.g., 20, 30, 40, 50, 60, 70, 80, 90, 100, 110, 120, 130, 140, 150 or 160) IU per day. In another embodiment, an oxytocin peptide is administered intranasally at a dose of about 40-100 IU per day. The dosing may be one or more times per day. The dosing may continue for several days, weeks, months or years. In another embodiment, the oxytocin peptide is administered as an adjunctive therapy to standard/current therapy for schizophrenia. In yet another embodiment, the oxytocin peptide is administered chronically or long term for at least 3 weeks or longer at least twice a day as described above. In yet other embodiments, the oxytocin peptide may be administered intraperitoneally, intravascularly, intramuscularly, orally, and the like, in either delayed or sustained release formulations or immediate release formulations.

The disclosure also provides a method of treating memory loss, memory function, recall, memorization, improvement in memory in Alzheimer's disease or other memory function disorder by administering to a subject in need of such treatment an effective amount of an oxytocin peptide. In one embodiment, the subject is a subject presenting with characterists schizophrenia or having schizophrenia. The oxytocin peptide may be a naturally occurring purified form of oxytocin, a recombinant for of oxytocin and analog of oxytocin, a chemically modified form of oxytocin or a combination thereof. In one embodiment, the oxytocin peptide is administered intranasally, mucosally, sublingually and the like. In one embodiment, the method comprises delivery an oxytocin peptide intranasally at least twice per day. In another embodiment, the oxytocin peptide is delivered at least twice per day at a dose of about 20-40 IU (international units) per administration (e.g., about 40-100 IU per day). In another embodiment, an oxytocin peptide is administered intranasally at a dose of about 40-100 IU per day. The dosing may be one or more times per day. The dosing may continue for several days, weeks, months or years. In yet another embodiment, the oxytocin peptide is administered chronically or long term for at least 3 weeks or longer at least twice a day as described above. In yet other embodiments, the oxytocin peptide may be administered intraperitoneally, intravascularly, intramuscularly, orally, and the like, in either delayed or sustained release formulations or immediate release formulations.

Impairments in cognitive performance and memory have been reported in humans treated with oxytocin, accordingly, the data presented herein is unexpected. To examine memory function two memory tasks, the California Verbal Learning Test (CVLT) and Letter Number Sequencing (LNS) task from the WAIS-III, were used to examine the potential effect on memory and learning. The disclosure demonstrates that oxytocin peptide administration intranasally at least twice per day (e.g., 20-40 IU per administration) as a primary therapy or adjunctive therapy improves non-social memory (e.g., non-socially relevant memory) in subjects. This is unexpected. Prior research studies have found that oxytocin had no effect or worsening of word memory devoid of social relevance. It has been recognized that oxytocin is a peptide that regulates social affiliation thus it is the role of oxytocin for enhancing social recognition and bonding is expected. However, the role of oxytocin in non-social relevant memory is totally unexpected based upon the prior research.

As used herein socially relevant memory would be memory for socially-relevant stimuli. Socially relevant stimuli would be any stimuli that have a socially relevant connotation. For example, socially relevant stimuli include human faces, words such as "love" or "hate". Socially relevant stimuli include stimuli that include an emotional state of bonding between humans. In contrast socially neutral stimuli would include a non-social object such as table, or words such as envelope, sky, numbers and the like. The disclosure provides methods of improving word memory and non-human object memory.

Thus, the methods of the disclosure comprise treating a mammal including a human with an amount of oxytocin peptide that stimulates memory function or treats a disease associated with memory inhibition or reduction. Further, the disclosure provides methods and composition for treating psychiatric disorders including schizophrenia. In one embodiment, the methods comprise administering an oxytocin peptide intranasally. In another embodiment, the method comprises administering the oxytocin mucosally such as sublingually. In yet other embodiments, the oxytocin peptide may be administered intraperitoneally, intravascularly, intramuscularly, orally, and the like, in either delayed or sustained release formulations or immediate release formulations.

The effect or an effective dose of oxytocin peptide can be measured using various recognized testing methods. For example, the CVLT-II is a commonly-used test of new learning and declarative verbal memory, which closely resembles the HVLT (Hopkins Verbal Learning Test), a part of the standardized MATRICS cognitive battery, now used to measure cognitive changes in Schizophrenia clinical trials. In the CVLT-II, a list of 16 words (List A) from various semantic categories are read over 5 trials. After each trial, subject is asked to recall as many words as they can (free recall). An interference list (List B) is then presented. Free and cued recall of List A is measured immediately following (short delay) and 20 minutes (long delay). At the end of the test, a 44 word recognition task is performed with subjects identifying target words among 28 distractors. The CVLT's format allows assessment of multiple aspects of cognition: overall recall ability, rate of learning over sequential trials, ability to retain learned material, and item recognition.

The Letter Number Sequencing subtest (LNS) is a component of the larger WAIS-III and is used to measure attention and working memory. It is similar to the Letter number span test, which is also part of the MATRICS. In each trial of the LNS, a list of letters and numbers are read in a mixed order to participants; participants are asked to recall first the digits and then the letters in the order they were presented. Length of the list ranges from 2 to 8; each length is tested three times. Scores are calculated by totaling the correct responses for each length.

A psychiatric or neurological disorder that may be treated by the methods of the disclosure include pervasive developmental disorder not otherwise specified, non-verbal learning disabilities, autism and autism spectrum disorders, attention deficit hyperactivity disorder (ADHD), anxiety disorders, Post-traumatic stress disorders, social phobia, generalized anxiety disorder, social deficit disorders, schizotypal personality disorder, schizoid personality disorder, schizophrenia, cognitive deficit disorders, dementia, Alzheimer's and other memory deficit disorders. In the methods of the disclosure such psychiatric or neurological disorders may be treated by administering an oxytocin peptide intranasally at least twice per day at a dose of about 20-40 IU per administration. In another embodiment, the dosing is 40 IU per administration or about 100 IU per day. In another embodiment, the dosing is continued for several days, weeks or years. In yet another embodiment, the psychiatric or neurological disorder is treated by improving non-social relevant memory capabilities. In yet other embodiments, the oxytocin peptide may be administered intraperitoneally, intravascularly, intramuscularly, orally, and the like, in either delayed or sustained release formulations or immediate release formulations.

The disclosure also provides a method of improving non-social memory capabilities in a normal subject, wherein the memory of the subject treated with an oxytocin peptide is improved compared to the same subject or a different subject not treated with oxytocin. In this embodiment of the disclosure a subject is treated to improve non-social memory by administering an oxytocin peptide intranasally at a dose of about 40-100 IU per day. The dosing may be one or more times per day. The dosing may continue for several days, weeks, months or years. In yet other embodiments, the oxytocin peptide may be administered intraperitoneally, intravascularly, intramuscularly, orally, and the like, in either delayed or sustained release formulations or immediate release formulations.

The disclosure also provides a method of treating metabolic disorders comprising intranasally delivering oxytocin peptide to a subject. The oxytocin peptide may be a naturally occurring purified form of oxytocin, a recombinant for of oxytocin and analog of oxytocin, a chemically modified form of oxytocin or a combination thereof. In one embodiment, the oxytocin peptide is administered intranasally, mucosally, sublingually and the like. The administration results in a reduction of blood glucose and weight loss. Metabolic diseases and disorders that may be treated by the methods of the disclosure include diabetes and obesity. By "treat" means reduction or modulation of a symptom of the disease. For example, administration of oxytocin intranasally can result in a reduction of blood glucose in diabetic patients or a reduction of weight in obese subjects. Such administration is recurring and typically long term. In one embodiment, an oxytocin peptide is administered intranasally at a dose of about 40-100 IU per day. The dosing may be one or more times per day (e.g., 2, 3, 4, 5, 6 times per day). The dosing may continue for several days, weeks, months or years. In yet other embodiments, the oxytocin peptide may be administered intraperitoneally, intravascularly, intramuscularly, orally, and the like, in either delayed or sustained release formulations or immediate release formulations.

Oxytocin peptides or their salts can be formulated for deliver by admixture with pharmaceutically acceptable non-toxic excipients or carriers. Mention may be made, as examples of pharmaceutically acceptable salts, of the addition salts with inorganic or organic acids (such as acetate, trifluoroacetate, propionate, succinate, benzoate, fumarate, maleate, oxalate, methanesulphonate, isethionate, theophyllinacetate, salicylate, methylenebis-.beta.-oxynaphthoate, hydrochloride, sulphate, nitrate and phosphate), the salts with alkali metals (sodium, potassium or lithium) or with alkaline-earth metals (calcium or magnesium), the ammonium salt or the salts of nitrogenous bases (ethanolamine, trimethylamine, methylamine, piperidine, benzylamine, N-benzyl-.alpha.-phenethylamine, choline, arginine, leucine, lysine or N-methylglucamine).

The disclosure provides pharmaceutical compositions of oxytocin peptides or their salts. The oxytocin peptide or their physiologically acceptable salts or solvates, may be formulated for administration for injection, or for oral, topical, nasal, inhalation, insufflation (either through the mouth or the nose) buccal, parenteral, rectal administration or other forms of administration. The disclosure provides pharmaceutical compositions comprising effective amounts of an oxytocin peptide together with pharmaceutically acceptable diluents, preservatives, solubilizers, emulsifiers, adjuvants, excipients and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol).

The compositions may also be incorporated into particulate preparations of polymeric compounds such as polylactic acid, polyglycolic acid, and the like or liposomes. Hyaluronic acid may also be used. Biocompatible absorbable polymers may be selected from the group consisting of aliphatic polyesters, copolymers and blends, which include, but are not limited to, homopolymers and copolymers of lactide (which include D-, L-, lactic acid and D-, L- and meso lactide), glycolide (including glycolic acid), epsilon-caprolactone, p-dioxanone (1,4-dioxan-2-one), alkyl substituted derivatives of p-dioxanone (i.e., 6,6-dimethyl-1,4-dioxan-2-one), triethylene carbonate (1,3-dioxan-2-one), alkyl substituted derivatives of 1,3-dioxanone, delta-valerolactone, beta-butyrolactone, gamma-butyrolactone, epsilon-decala tone, hydroxybutyrate, hydroxyvalerate, 1,4-dioxepan-2-one and its dimer 1,5,8,12-tetraoxacyclotetradecane-7,14 dione, 1,5-dioxepan-2-one, and polymer blends thereof.

Such compositions may influence physical state, stability, rate of in vivo release, and rate of in vivo clearance. See, e.g., Remington s Pharmaceutical Sciences, 18th ed., (1990, Mack Publishing Co., Easton, Pa. 18042) pages 1435-1712). The compositions may be prepared in liquid form, or be in dried powder, such as lyophilized form.

Contemplated for use herein are oral solid dosage forms, which are disclosed generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets or pellets. Also, liposomal or proteinoid encapsulation may be used to formulate compositions. Liposomal encapsulation may be used and the liposomes may be derivatized with various polymers. A description of possible solid dosage forms for the therapeutic is given by Marshall, K. In: Modern Pharmaceutics Edited by G. S. Banker and C. T. Rhodes Chapter 10, 1979). In general, the formulation will include an Oxytocin peptide and inert ingredients (which allow for protection against the stomach environment and release of the biologically active material in the intestine).

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L3OD, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic, i.e., powder; for liquid forms, a soft gelatin shell may be used. The shell material of cachets may be thick starch or other edible paper. For pills, lozenges, molded tablets or tablet triturates, moist massing techniques can be used.

The therapeutic can be included in the formulation as fine multi-particulates in the form of granules or pellets. The formulation of the material for capsule administration can also be as a powder, lightly compressed plugs or even as tablets. The therapeutic can also be prepared by compression.

Colorants and flavoring agents may all be included. For example, the peptide (or derivative) may be formulated (such as by liposome or microsphere encapsulation) and then further contained within an edible product, such as a refrigerated beverage containing colorants and flavoring agents.

One may dilute or increase the volume of the therapeutic with an inert material or filler. These diluents or fillers can include carbohydrates, especially mannitol, anhydrous lactose, cellulose (e.g., microcrystalline cellulose), sucrose, calcium hydrogen phosphate modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch (e.g., potato starch or the commercial disintegrant based on starch, Explotab). Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch (e.g., pregelatinised maize starch) and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes, talc and silica. Soluble lubricants may also be used such as sodium lauryl sulfate, magnesium lauryl sulfate, polyethylene glycol of various molecular weights, Carbowax 4000 and 6000.

Glidants that can improve the flow properties of the drug during formulation and to aid rearrangement during compression can be added. The glidants can include starch, talc, pyrogenic silica and hydrated silicoaluminate.

To aid dissolution of the therapeutic into the aqueous environment a surfactant can be added as a wetting agent. Surfactants may include anionic detergents such as sodium lauryl sulfate, dioctyl sodium sulfosuccinate and dioctyl sodium sulfonate. Cationic detergents can be used and can include benzalkonium chloride or benzethomium chloride. The list of potential non-ionic detergents that can be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants can be present in the formulation of the protein or derivative either alone or as a mixture in different ratios.

Additives that potentially enhance uptake of the agent are, for example, the fatty acids oleic acid, linoleic acid and linolenic acid.

Controlled release oral formulation may be desirable. The agent can be incorporated into an inert matrix that permits release by either diffusion or leaching mechanisms, e.g., gums. Slowly degenerating matrices may also be incorporated into the formulation. Some enteric coatings also have a delayed release effect.

Other coatings may be used for the formulation. These include a variety of sugars that can be applied in a coating pan. The therapeutic agent can also be given in a film coated tablet and the materials used in this instance are divided into two groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials can be used to provide the optimum film coating. Film coating may be carried out in a pan-coater or in a fluidized bed or by compression coating.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

The Oxytocin peptides may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations disclosed previously, the oxytocin peptides may also be formulated as a depot preparation. Such long acting formulations may be administered by implantation (for example subcutaneously or intramuscularly) or by intramuscular injection. Thus, for example, the Oxytocin peptides may be formulated with suitable polymeric or hydrophobic materials (for example as an emulsion in an acceptable oil) or ion exchange resins, or as sparingly soluble derivatives, for example, as a soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Toxicity and therapeutic efficacy of such oxytocin peptides can be determined by standard pharmaceutical procedures in cell cultures or experimental animal/animal models (such as those described herein), e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies within a range of circulating concentrations that include the ED50 with little or no toxicity. The dosage may vary within this range depending upon the dosage form employed and the route of administration utilized. A dose may be formulated in animal models to achieve a circulating plasma concentration range that includes the IC.sub.50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An oxytocin peptide and components of a therapeutic composition may be introduced parenterally, topically, or transmucosally, e.g., orally, nasally, or rectally, or transdermally. Parenteral administration includes, for example, intravenous injection, intra-arteriole, intramuscular, intradermal, subcutaneous, intraperitoneal, intraventricular, and intracranial administration.

Because many oxytocin peptide are capable of crossing the blood brain barrier oxytocin peptides permit oral, parenteral or intravenous administration. Alternatively, the agent can be modified or otherwise altered so that it can cross or be transported across the blood brain barrier. Many strategies known in the art are available for molecules crossing the blood-brain barrier, including but not limited to, increasing the hydrophobic nature of a molecule; introducing the molecule as a conjugate to a carrier, such as transferring, targeted to a receptor in the blood-brain barrier, or to docosahexaenoic acid and the like.

In another embodiment, an Oxytocin peptide may be administered by surgical intervention including a procedure of drilling a small hole in the skull to administer the agent.

In another embodiment, the molecule can be administered intracranially or intraventricularly. In another embodiment, osmotic disruption of the blood-brain barrier can be used to effect delivery of agent to the brain (Nilayer et al., Proc. Natl. Acad. Sci. USA 92:9829-9833 (1995)). In yet another embodiment, an agent can be administered in a liposome targeted to the blood-brain barrier. Administration of pharmaceutical agents in liposomes is known (see Langer, Science 249:1527-1533 (1990); Treat et al., in Liposomes in the Therapy of infectious Disease and Cancer, Lopez-Berestein and Fidler (eds.), Liss, New York, pp. pp. 317-327 and 353-365 (1989).

Some predictions have been made concerning the ability of molecules to pass through the blood-brain barrier, the rate and extent of entry of an oxytocin peptide or a formulation comprising an oxytocin peptide into the brain are generally considered to be determined by partition coefficient, ionization constant(s), and molecular size.

In another embodiment, a therapeutic formulation comprising an oxytocin peptide can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 317-327 and 353-365 (1989)).

In another embodiment, a therapeutic formulation comprising an oxytocin peptide can be delivered in a controlled release system. For example, the oxytocin peptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In addition, any of the materials described herein can be administered to any part of the mammal's body including, without limitation, brain, spinal fluid, blood stream, lungs, nasal cavity, intestines, stomach, muscle tissues, skin, peritoneal cavity, and the like. Thus, an oxytocin peptide (e.g., a neurotensin analog) can be administered by intravenous, intraperitoneal, intramuscular, subcutaneous, extracranial, intrathecal, and intradermal injection, by oral administration, by inhalation, or by gradual perfusion over time. For example, an aerosol preparation can be given to a mammal by inhalation. It is noted that the duration of treatment with the materials described herein can be any length of time from as short as one day to as long as a lifetime (e.g., many years). For example, a formulation comprising an oxytocin peptide can be administered once (or twice, three times, etc.) daily, weekly, monthly, or yearly.

Preparations for administration can include sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water as well as alcohol, saline, and buffered solutions. Preservatives, flavorings, and other additives such as, for example, antimicrobials, anti-oxidants, chelating agents, inert gases, and the like may also be present.

An oxytocin peptide or a pharmaceutical composition comprising an oxytocin peptide may be dispensed intranasally or mucosally as a powdered or liquid nasal spray, suspension, nose drops, a gel, film or ointment, through a tube or catheter, by syringe, by packtail, by pledget (a small flat absorbent pad), by nasal tampon or by submucosal infusion. Nasal drug delivery can be carried out using devices including, but not limited to, unit dose containers, pump sprays, droppers, squeeze bottles, airless and preservative-free sprays, nebulizers (devices used to change liquid medication to an aerosol particulate form), metered dose inhalers, and pressurized metered dose inhalers. It is important that the delivery device protect the drug from contamination and chemical degradation. The device should also avoid leaching or absorption as well as provide an appropriate environment for storage. Each drug needs to be evaluated to determine which nasal drug delivery system is most appropriate. Nasal drug delivery systems are known in the art and several are commercially available.

An oxytocin peptide or a pharmaceutical composition comprising an oxytocin peptide may be conveniently delivered in the form of an aerosol spray using a pressurized pack or a nebulizer and a suitable propellant including, but not limited to, dichlorodifluoromethane, trichlorofluoromethane, dichlorotetrafluoroethane, hydrocarbons, compressed air, nitrogen or carbon dioxide. An aerosol system requires the propellant to be inert towards the pharmaceutical composition. In the case of a pressurized aerosol, the dosage unit may be controlled by providing a valve to deliver an accurately metered amount.

The means to deliver an oxytocin peptide or pharmaceutical composition comprising an oxytocin peptide to the nasal cavity as a powder can be in a form such as microspheres delivered by a nasal insufflator device (a device to blow a gas, powder, or vapor into a cavity of the body) or pressurized aerosol canister. The insufflator produces a finely divided cloud of the dry powder or microspheres. The insufflator may be provided with means to ensure administration of a substantially metered amount of the pharmaceutical composition. The powder or microspheres should be administered in a dry, air-dispensable form. The powder or microspheres may be used directly with an insufflator which is provided with a bottle or container for the powder or microspheres. Alternatively the powder or microspheres may be filled into a capsule such as a gelatin capsule, or other single dose device adapted for nasal administration. The insufflator can have means such as a needle to break open the capsule or other device to provide holes through which jets of the powdery composition can be delivered to the nasal cavity.

Nasal delivery devices can be constructed or modified to dispense an oxytocin peptide or a pharmaceutical composition comprising an oxytocin peptide wherein the oxytocin peptide or the composition is delivered predominantly to the inferior two-thirds of the nasal cavity. For example, the angle of dispersion from a delivery device such as a nebulizer or an insufflator can be set so that the pharmaceutical composition is mechanically directed to the inferior two-thirds of the nasal cavity, and preferably away from the superior region of the nasal cavity. Alternatively, an oxytocin peptide or a pharmaceutical composition comprising an oxytocin peptide can be delivered to the inferior two-thirds of the nasal cavity by direct placement of the composition in the nasal cavity, for example, with a gel, an ointment, a nasal tampon, a dropper, or a bioadhesive strip.

Thus in some embodiments of the disclosure, the methods comprise administering to an individual an oxytocin peptide or pharmaceutical composition comprising an oxytocin peptide wherein administration to the nasal cavity is by a nasal delivery device. The nasal delivery device can include, but is not limited to, unit dose containers, pump sprays, droppers, squeeze bottles, airless and preservative-free sprays, nebulizers, dose inhalers, pressurized dose inhalers, insufflators, and bi-directional devices. The nasal delivery device can be metered to administer an accurate effective dosage amount to the nasal cavity. The nasal delivery device can be for single unit delivery or multiple unit delivery. In some embodiments of the disclosure, the nasal delivery device can be constructed whereby the angle of dispersion of a pharmaceutical composition is mechanically directed towards the inferior two-thirds of the nasal cavity thereby minimizing delivery to the olfactory region. In some embodiments of the disclosure, the nasal delivery device may be activated only on exhalation, thus limiting the inhalation induced and potentially undesirable distribution of the pharmaceutical composition. In some embodiments of the disclosure, the pharmaceutical composition is a gel, film, cream, ointment, impregnated in a nasal tampon or bioadhesive strip whereby the composition is placed in the inferior two-thirds of the nasal cavity. In some embodiments of the disclosure, the methods include intranasal administration of an oxytocin peptide or a pharmaceutical composition comprising an oxytocin peptide wherein the administration uses a nasal delivery device with an angle of dispersion that mechanically directs the agent to the inferior two-thirds of the nasal cavity wherein the oxytocin peptide is administered after a vasoconstrictor. In some embodiments of the disclosure, the methods include intranasal administration of an oxytocin peptide or pharmaceutical composition comprising an oxytocin peptide wherein the administration uses a nasal delivery device with an angle of dispersion that mechanically directs the agent to the inferior two-thirds of the nasal cavity wherein the oxytocin peptide is co-administered with a vasoconstrictor.

As used herein, "mucosal administration" or "administered transmucosally" refers to delivery to the mucosal surfaces of the nose, nasal passageways, nasal cavity; the mucosal surfaces of the oral cavity including the gingiva (gums), the floor of the oral cavity, the cheeks, the lips, the tongue, the teeth; and the mucosal surfaces of or around the eye including the conjunctiva, the lacrimal gland, the nasolacrimal ducts, the mucosa of the upper or lower eyelid and the eye.

Intranasal drug delivery has been a topic of research and development for many years, although it has been only within the past decade that carrier systems have been devised which make delivery of substances effective. (Sayani and Chien (1996) Critical Reviews in Therapeutic Drug Carrier Systems, 13:85-184). Intranasal delivery has a number of advantageous features including comparatively high bioavailability, rapid kinetics of absorption and avoidance of a first-pass effect in the liver. In regard to patient compliance and ease of use, intranasal administration provides a simple, rapid and non-invasive mode of application. In some embodiments, intranasal administration can allow for delivery of an oxytocin peptide to the nasal cavity and in other embodiments, intranasal administration can allow for targeted delivery to the trigeminal nerve. Targeted delivery to the trigeminal nerve and preferably not the olfactory region can reduce the amount of drug entering the CNS or systemic circulation thereby reducing or eliminating potential undesirable CNS effects or systemic side effects. Targeted delivery to the trigeminal nerve can also reduce the effective dosage necessary to achieve analgesia in the facial or head regions wherein lower effective dosages will further reduce any potential CNS or systemic side effects.

As used herein, "intranasal administration" or "administered intranasally" refers to delivery to the nose, nasal passageways or nasal cavity by spray, drops, powder, gel, film, inhalant or other means.

The nasal cavity contains turbinate bones which protrude into the nasal cavity and generally separate it into three regions. As used herein, the "inferior region of the nasal cavity" refers to the portion of the nasal cavity where the middle and inferior turbinate bones protrude and is a region of the nasal cavity that is innervated by the trigeminal nerve system. The superior area of the nasal cavity is defined by the superior turbinate bone wherein the olfactory region is located.

An oxytocin peptide is administered in a dose sufficient to provide a therapeutically effective amount to an individual to promote memory recall, to reduce blood glucose levels or to treat schizophrenia. A therapeutically effective dose of an oxytocin peptide can be determined empirically and depends on the type of treatment (e.g., reducing blood glucose), the route of administration, and the size, weight, age and overall health of the patient, as is within the skill of one in the art such as a medical practitioner.

The amount of an oxytocin peptide administered as a unit dose will depend upon the type of pharmaceutical composition being administered, for example, a solution, a suspension, a gel, a film, an emulsion, a powder, or a sustained-release formulation. In some examples, the effective dosage will be lower than dose amounts needed for oral, intravenous, intramuscular or subcutaneous administration, since transmucosal or transdermal delivery may allow for a more concentrated level of the oxytocin peptide within the facial and head region. The quantity of formulation needed to deliver the desired dose will also depend on the concentration of the oxytocin peptide in the composition. Such determinations are within the skill of one in the art.

The therapeutic dosage of an oxytocin peptide in the pharmaceutical compositions used in the methods of the disclosure will depend on a number of factors such as the chemical composition and/or modification of the oxytocin peptide, its bioavailability by the chosen route of administration, its efficacy, the desired frequency of administration combined with the desired single dosage of the formulation and whether the oxytocin peptide is administered in combination with other active agent(s). Particularly, the dosage of an oxytocin peptide will be chosen to maximize memory recall or a desired blood glucose level. Pharmacological data can be obtained from animal models and clinical trials with normal human volunteers or patients by one with skill in the art.

As stated above, an effective amount of an oxytocin peptide will depend on the form and composition being used in the method. For example, dosages used for administration of an oxytocin peptide can include, but are not limited to, an effective amount within the dosage range of about 0.1 IU to about 150 IU, or within 1 IU to about 100 IU, or within 10 IU to about 100 IU, or within about 25 IU to about 50 IU, or within about 1 IU to about 40 IU, or within about 1 IU to about 30 IU, or within about 4 IU to about 16 IU, or within about 4 IU to about 24 IU.

Dosages can be administered in a single dose or in multiple doses, for example, dosages can be administered two, three, four, up to ten times daily depending on the type of treatment as well as on individual susceptibility. Dosages can be administered in a sustained release formulation which may allow for an oxytocin peptide to be administered less frequently such as six times a week, five times a week, four times a week, three times a week, twice a week, or once a week, once a month, once every two months, three months, four months, five months or six months or more. Infrequent administration can be accomplished by sustained release formulations.

In some embodiments of the disclosure, a composition comprising an oxytocin peptide may further comprise an additional active agent, wherein the oxytocin peptide and the additional active agent(s) are administered as a mixture, separately and simultaneously, or separately in any order. In some examples the composition comprising an oxytocin peptide is administered in combination with at least one additional active agent. In other examples, the composition comprising an oxytocin peptide is administered in combination with at least two additional active agents.

In one embodiment, the disclosure allows for the treatment of patients with a memory disease or disorder (e.g., Alzheimer's Disease). In another embodiment, the disclosure allows for the treatment of patients with a high glucose levels.

As used herein, the term "memory improving amount", or "glucose lowering amount," or "effective amount" means the amount of a composition comprising an oxytocin peptide or analogue useful for causing an improvement in memory recall compared to memory recall prior to receiving an effective amount of oxytocin or analogue thereof or a diminution in blood glucose levels.

The following example is provided in illustration of the disclosure and should not be construed in any way as constituting a limitation thereof.

EXAMPLES

Example 1

Participants. Subjects with a DSM-IV diagnosis of schizophrenia, confirmed by SCID interview, were enrolled in this double-blind, placebo-controlled, crossover study. Other main inclusion criteria were: minimum 18 years of age, treatment with 1 or 2 approved antipsychotic medication with no dose changes in the previous four weeks, Positive and Negative Syndrome Scale (PANSS) score of at least 55 and a Clinical Global Impressions-Severity (CGI-S) scale score of at least 4 (moderately ill) at randomization. Because it was hypothesized that oxytocin may improve paranoia due to its pro-trust effect, subjects were also required to have a score of at least 4 (moderate) on item 6 (suspiciousness/persecution) of the PANSS. This study was approved by the UCSD IRB and written informed consent was obtained from all subjects.

Study Drugs. Subjects were maintained on their pre-study antipsychotic medication regimen and doses were not changed during the study. Subjects received 3-weeks of daily intranasal oxytocin (Syntocinin, Novartis, Basel Switzerland) and 3-weeks of daily intranasal placebo. Oxytocin was dosed at 20 IU (5 sprays) twice a day for the first week and 40 IU (10 sprays) twice a day thereafter. Order of treatment (placebo-oxytocin or oxytocin-placebo) was randomly assigned using a computer generated random sequence.

Efficacy and Safety assessments. Subjects, raters and study staff enrolling patients were blinded to treatment condition. The total study duration for each individual subject was 7 weeks. Subjects were evaluated 7 times. Visit 1 and 5 were baseline assessments and visits 2, 3, 4 and 6, 7, 8 were the weekly visits for the two treatment periods, respectively. Washout occurred in the week between visit 4 and 5. At each visit raters assessed subjects utilizing the PANSS, CGI-S and CGI-Improvement (CGI-I). PANSS-total at the final visit of each treatment period was chosen a' priori as the primary efficacy endpoint.

Safety was assessed at each visit by a medical exam, and assessments of reported adverse events. In addition, urine was collected for osmolality testing and blood was drawn at each visit and analyzed at UCSD laboratories for basic chemistry analysis. Statistical Methods. Data from all subjects who received at least one dose and one assessment in both treatment periods (intent-to-treat population) were subjected to analysisusing SPSS version 11.0. Baseline scores for both drug treatments were compared for similarity using paired t-test. The change in baseline scores from period 1 to period 2 was compared among the placebo-oxytocin versus oxytocin-placebo group using a two-sample t-test to assess for period carry-over effects. PANNS and CGI data were subjected to repeated measures ANOVA with drug and treatment-week as repeated measures factors. Treatment sequence was included as a between-subjects factor to evaluate possible period and carry-over effects. Paired t-tests, corrected for multiple-comparisons using Bonferoni method were used to compare placebo and oxytocin scores at endpoint and each the other assessment visits. Cohen's d statistic was calculated for each measure at endpoint.

Fifteen of 19 randomized subjects completed all study visits. Four randomized subjects were discontinued before completing the study, one due to nasal discomfort from the intranasal sprays, 3 due to insufficient compliance. None of the discontinued subjects reached the second treatment period, therefore, intent-to-treat population was identical to completer population. Eighty percent of completers were male, 53% black, 27% white, average age was and duration of disease was 48 (8.9) and 26 (14.6), respectively (Table 1). They were on a wide range of antipsychotics entering the study (table 2).

TABLE 1

Demographics of completers

|  | N | % |
|---|---|---|
| Gender |  |  |
| Male | 12 | 80% |
| Female | 3 | 20% |
| Race |  |  |
| Caucasian | 4 | 26.70% |
| Black | 8 | 53.30% |
| Other | 3 | 20% |
| Initial Treatment |  |  |
| Oxytocin | 6 | 40% |
| Placebo | 9 | 60% |
| Age (STD) | 48 | (8.9) |
| Average years ill (STD) | 25.8 | (14.5) |

TABLE 2

Antipsychotics Subjects Received Prior to and During Study

| Drug type | N |
|---|---|
| Quetiapine | 6 |
| Aripiprazole | 4 |
| Risperidone | 4 |
| Olanzapine | 2 |
| Ziprasidone | 1 |
| Chlorpromazine | 1 |

Table 3 lists efficacy results. Baseline scores at the start of each placebo and oxytocin treatment arm were highly similar for PANSS-total (82.1±11.06 and 81.4±12.43) and CGI-S (4.60±0.74 and 4.67±0.74). Change in scores between first period and second period baselines did not significantly differ between groups, suggesting there wasn't significant carry-over.

TABLE 3

Efficacy Scores (±Standard Deviation)

|  | Baseline | Week 1 | Week 2 | Week 3 [Cohen's d]# |
|---|---|---|---|---|
| PANSS Total |  |  |  |  |
| Placebo | 82.1 (11.1) | 76.9 (10.6) | 75.7 (12.7) | 79.1 (12.9) |
| Oxytocin | 81.5 (12.4) | 76.3 (11.3) | 76.9 (13.2) | 73.6 (13.6)** [0.43] |
| PANSS Positive |  |  |  |  |
| Placebo | 22.8 (5.2) | 21.2 (5.0) | 20.0 (4.6) | 21.9 (4.8) |
| Oxytocin | 21.7 (4.1) | 20.6 (4.5) | 20.5 (4.6) | 19.9 (5.2)** [0.40] |
| PANSS Negative |  |  |  |  |
| Placebo | 21.8 (4.7) | 20.5 (4.4) | 20.2 (4.6) | 20.7 (4.3) |
| Oxytocin | 20.2 (4.7) | 20.1 (4.8) | 19.7 (4.3) | 18.5 (4.5)* [0.50] |
| PANSS Gen. Psy. |  |  |  |  |
| Placebo | 37.5 (6.6) | 35.2 (6.2) | 35.4 (7.3) | 36.4 (7.3) |
| Oxytocin | 38.8 (7.6) | 36.4 (8.1) | 36.3 (8.2) | 34.8 (6.9) [0.24] |
| PANSS CGI-I |  |  |  |  |
| Placebo | 4.60 (0.74)^ | 3.53 (0.92) | 3.53 (0.92) | 3.73 (1.03) |
| Oxytocin | 4.67 (0.61)^ | 3.33 (0.62) | 3.33 (1.20) | 3.07 (0.70)** [0.74] |

Significantly different Vs. Placebo *P < 0.05, **P < 0.01
0.2 small, 0.5 medium, 0.8 large;
^CGI-Severity and not CGI-Improvement noted for baseline There was a significantly greater improvement in PANSS-total scores across visits with oxytocin compared to placebo as revealed by a significant Drug-by-Treatment Week interaction ($F(2,26)=6.493$, $p=0.005$). None of the other main or interaction effects were significant. Scores were significantly lower with oxytocin versus placebo at the endpoint (week 3) visit (diff.=5.46, $p<0.001$, Cohen d effect size=0.43) whereas there was no significant difference at baseline (difference=0.60), week 1 (difference=0.60) or week 2 (difference=1.20).

CGI-I scores revealed a Drug-by-Treatment Week interaction that approached significance ($P=0.065$, Cohen's $d=0.74$). No other main or interaction effect was significant. CGI-I was significantly lower for oxytocin versus placebo at week 3 ($P<0.001$) but not at baseline, week 1, or week 2.

Analysis of PANSS negative subscale scores did not reveal any significant main factor or interaction effects but were significantly lower for oxytocin versus placebo at week 3 only ($p=0.023$, Cohen's $d=0.50$).

A greater decrease in PANSS positive subscale scores under oxytocin was reflected in a non-significant trend toward a Drug-by-Treatment Week interaction ($p=0.089$). There was also a significant Drug by Treatment Sequence effect ($F(1.13)=11.57$, $p=0.005$) reflected in the fact that PANSS positive scores were significantly lower with oxytocin treatment ($P=0.01$) when it was the first treatment but not when it was the second treatment. There were no other significant main or interaction effects. Oxytocin scores were significantly lower than placebo scores at week 3 ($P=0.006$, Cohen's $d=0.4$) but not at baseline, week 1 or week 2.

A greater decrease in PANSS general psychopathology subscale under oxytocin was reflected in a non-significant trend toward a Drug-by-Visit interaction ($p=0.069$, Cohen's $d=0.24$). Oxytocin scores were not significantly different than placebo at any time point.

Overall, differences in the first period by itself (between subjects analysis) did not reach statistical significance.

There were no serious adverse events reported during the study and no significant differences in rates of reported adverse effects with oxytocin compared to placebo (Table 4), There was no significant differences between oxytocin and placebo in any of the measured blood chemistry or urine osmolality (Table 5).

TABLE 4

Reported Adverse Events

|  | Oxytocin (n) | Placebo (n) |
|---|---|---|
| Headache | 26.7% (4) | 20.0% (3) |
| Dyspepsia or nausea | 26.7% (4) | 40.0% (6) |
| Sleep impairment | 33.3% (5) | 26.7% (4) |
| Dizzy or lightheaded | 26.7% (4) | 20.0% (3) |

TABLE 4-continued

Reported Adverse Events

|  | Oxytocin (n) | Placebo (n) |
|---|---|---|
| Nasal Irritation | 26.7% (4) | 13.3% (2) |
| Lethargy | 0.0% (0) | 13.3% (2) |

TABLE 5

Chemistry analysis at endpoint

|  | Glucose (mg/dL) | BUN (mg/dL) | Creatinine (mg/dL) | Bicarb. (mmol/L) | Chloride (mmol/L) | Sodium (mmol/L) | Potassium (mmol/L) | Calcium (mg/dL) | Urine Osmolality (mOsm/kg) |
|---|---|---|---|---|---|---|---|---|---|
| Oxytocin | 112.5 | 10.8 | 0.9 | 27.9 | 101.1 | 138.5 | 4.4 | 9.3 | 607.9 |
| Placebo | 128.9 | 10 | 0.9 | 27.4 | 100.8 | 138.5 | 4.2 | 9.3 | 557.6 |

The disclosure demonstrates that 3 weeks of intranasal oxytocin, given adjunctive to standard antipsychotic medications, caused significantly greater reductions in schizophrenia symptoms at the study endpoint compared to placebo. This result supports the hypothesis that oxytocin exhibits antipsychotic properties.

Oxytocin's effect appeared to manifest broadly across symptom clusters including positive and negative symptoms, although the improvement in positive symptoms appeared statistically more robust. Though the numerical effect of oxytocin is modest (7.9 point reduction on the PANSS-total compared to 3.0 points for placebo), three points regarding its observed magnitude of benefit warrant consideration. First, subjects were already on stable therapeutic doses of at least one antipsychotic and oxytocin represented adjunctive treatment. Compared to a medication-free cohort, improvements in this already-treated cohort are generally harder to come by. Notwithstanding this fact, the effect size of the improvements observed were medium ((0.43) PANSS scores) to large ((0.74) CGI-I). Second, this study had dosing and duration limitations that may have prevented the optimal magnitude of benefit from being observed: only one oxytocin dose was studied, and subjects were treated for only 3 weeks. Either higher doses or longer treatment duration may have yielded greater symptom improvements. Supporting this latter point, oxytocin's benefits emerged only at the week 3 assessment, a finding that suggests a delayed onset of action which may have grown with longer treatment duration. Finally, while it is possible that a certain subpopulation of schizophrenia patients is particularly responsive to the benefits of oxytocin (based on receptor variations or diagnostic subtype), the sample size was too small for a subanalysis along these lines. To fully characterize oxytocin's antipsychotic potential, future studies are warranted with larger sample sizes, different doses, longer treatment durations, as well as pharmacogenetic and behavioral investigations.

Despite its therapeutic potential, there have been very few trials of oxytocin for psychiatric conditions. As such, the finding that oxytocin—given twice daily for three weeks—was well-tolerated and did not appear to produce any subjective or objective adverse events is noteworthy.

The disclosure demonstrates that intranasal oxytocin, given adjunctive to standard antipsychotic medications, caused significantly greater reductions in schizophrenia symptoms at the study end point compared with placebo. In addition, the intranasal administration demonstrated an improvement in memory and a reduction in blood glucose levels compared to placebo.

Example 2

Participants. Subjects with a DSM-IV diagnosis of schizophrenia, confirmed by SCID interview, were enrolled in a double-blind, placebo-controlled, crossover study. Other main inclusion criteria were: minimum 18 years of age, treatment with 1 or 2 approved antipsychotic medication with no dose changes in the previous four weeks, a minimum Positive and Negative Syndrome Scale (PANSS) score of at least 55 with a minimum score of 4 and a Clinical Global Impressions-Severity (CGI-S) scale score of at least 4 (moderately ill) at randomization.

Study Drugs. Subjects were maintained on a stable dose of their pre-study antipsychotic medication regimen. In addition to their antipsychotics, subjects received 3-weeks of daily intranasal oxytocin (Syntocinin, Novartis, Basel Switzerland) dosed 20 IU twice a day for the first week and then 40 IU twice a day for weeks two and three, and 3-weeks of daily intranasal placebo. Order of treatment (placebo-oxytocin or oxytocin-placebo) was randomly assigned using a computer generated random sequence.

Safety and efficacy assessments. Subjects, raters, and study staff enrolling patients were blinded to treatment condition. The total study duration for each individual subject was 7 weeks, which included a baseline visit (V1), a three-week initial treatment period, a 1 week washout (between V4 and V5), a repeat baseline visit, and a three-week crossover treatment period. Subjects received the cognitive tests a total of 3 times: at baseline visits (V1, and after 3 weeks of treatment with placebo and oxytocin (V4, V7).

The CVLT-II is a commonly-used test of new learning and declarative verbal memory, which closely resembles the HVLT (Hopkins Verbal Learning Test), a part of the standardized MATRICS cognitive battery, now used to measure cognitive changes in Schizophrenia clinical trials. In the CVLT-II, lists of 16 words (List A) from various semantic categories are read over 5 trials. After each trial, subject is asked to recall as many words as they can (free recall). An interference list (List B) is then presented. Free and cued recall of List A is measured immediately following (short delay) and 20 minutes (long delay). At the end of the test, a 44 word recognition task is performed with subjects identifying target words among 28 distractors. The CVLT's format allows assessment of multiple aspects of cognition: overall recall ability, rate of learning over sequential trials, ability to retain learned material, and item recognition.

The Letter Number Sequencing subtest (LNS) is a component of the larger WAIS-III and is used to measure attention and working memory. It is similar to the Letter number span test, which is also part of the MATRICS. In each trial of the LNS, a list of letters and numbers are read in a mixed order to participants; participants are asked to recall first the digits and then the letters in the order they were presented. Length of the list ranges from 2 to 8; each length is tested three times. Scores are calculated by totaling the correct responses for each length.

For each subtest a two-factor repeated ANOVA with drug treatment (placebo/oxytocin) and order of treatment as factors was conducted.

Of the 20 subjects enrolled, 15 (12 males, 3 females) completed both treatment arms and thus provided CVLT and LNS data on both placebo and oxytocin. Average age was 48.0+/−8.9 years and had been ill an average of 25.8+/−14.5 years.

Subjects scored higher on all 9 subscales of the CVLT after 3 weeks of oxytocin than after placebo (Table 6). Oxytocin outperformed placebo regardless of the order oxytocin was given, obviating the possibility of a 'practice' effect.

TABLE 6

CLVT Data

| Test | Baseline Mean (S.E.M.) | Placebo Mean (S.E.M) | Oxytocin Mean (S.E.M.) |
|---|---|---|---|
| Trials 1-5 Raw | 45.0 (3.00) | 51.33 (4.51) | 55.67 (3.65) |
| Short Delay Free Recall Raw | 8.27 (0.88) | 9.47 (1.22) | 10.60 (1.03) |
| Short Delay Cued Recall Raw | 9.87 (0.87) | 10.87 (1.07) | 12.00 (0.79) |
| Long Delay Free Recall Raw | 9.07 (0.96) | 10.73 (0.85) | 10.87 (0.87) |
| Long Delay Cued Recall Raw | 10.0 (0.87) | 11.33 (1.04) | 11.87 (0.97) |
| Total Repetitions Raw | 8.73 (2.74) | 10.07 (4.71) | 13.67 (5.44) |
| Total Intrusions Raw | 6.53 (2.08) | 6.00 (1.94) | 4.93 (1.90) |
| Total Recall Discriminability Raw | 1.77 (0.17) | 2.05 (0.21) | 2.22 (0.19) |
| Total Recognition Discriminability Raw | 2.79 (0.21) | 2.63 (0.36) | 2.97 (0.28) |

In contrast to the CVLT findings, there was no significant difference on any of the scores on the LNS between oxytocin and placebo.

The disclosure provides evidence of beneficial effects of oxytocin on non-social cognition. Contrary to the original concern that oxytocin might have a negative effect on memory and learning, no deleterious effect of 3-weeks of daily oxytocin on either of the cognitive tests was observed. Surprisingly, oxytocin enhanced performance on all CVLT with a stronger enhancement of short-delay memory over long-delay memory.

It is noteworthy that the well-known "practice effect" phenomenon whereby repeat administration of cognitive tests produces enhanced performance was masked in this study by drug treatment effects. That is, the expected improvement in performance in the last test session (end of second treatment period) compared to the previous test administration (end of first treatment period) was only seen among subjects who received oxytocin when the last test was administered. Subjects who received placebo when the last test was administered exhibited a decrement in scores compared to their previous testing while receiving oxytocin.

In contrast to CVLT results, oxytocin did not have an effect on the LNS. Though this negative finding is important in that it addresses concerns that that repeated daily oxytocin administration may have a negative effect on working memory in patients with schizophrenia, it contrasts the positive effects of oxytocin seen in the CVLT. One possible explanation for these discrepant effects involves the different aspects of cognition assayed by the different tests. The CVLT is a test of verbal learning that uses whole words and therefore probes deeper lexical content, whereas the LNS is a less meaning-based measure of working memory using letters and digits, and invoking little semantic processing.

In studies using socially salient stimuli such as words relevant to relationship, reproduction or sex or photos of faces, the results have generally found a mnemonic effect in normal subjects after a single dose of oxytocin (24 IU) but at least one study found the opposite effect with socially-relevant words. In contrast previous studies have shown that when measuring memory for non-socially relevant stimuli, oxytocin has no effect or even worsens performance.

Because the CVLT uses neutral words (furniture", "vegetables", "ways of traveling", and "animal") but not social, sexual, or reproduction-related words the mnemonic effect of oxytocin in this study stands in contrast to previous findings, which found no effect or a worsening of memory for non-socially relevant stimuli.

The examples set forth above are provided to give those of ordinary skill in the art a complete disclosure and description of how to make and use the embodiments of the methods, treatments and compositions of the disclosure, and are not intended to limit the scope of what the inventors regard as their disclosure. Modifications of the above-described modes for carrying out the disclosure that are obvious to persons of skill in the art are intended to be within the scope of the following claims.

The invention claimed is:

1. A method for reducing blood glucose levels of a subject, the method comprising intranasally administering to the subject a formulation comprising an oxytocin peptide or analogue thereof at least once per day at a dose of about 20-100 IU, wherein the dose of oxytocin peptide or analogue thereof reduces a subject's blood glucose compared to the subject's blood glucose before administration of the oxytocin peptide or analogue thereof.

2. The method of claim 1, wherein the total daily dose is about 100 IU per day.

3. The method of claim 1, wherein the dose is at least two times per day.

4. The method of claim 1, wherein the dose is about 40-80 IU per day.

* * * * *